United States Patent [19]

Suwa et al.

[11] Patent Number: 5,374,713

[45] Date of Patent: Dec. 20, 1994

[54] PEPTIDE INHIBITORS OF PHOSPHOLIPASE $A_2$ PURIFIED FROM INFLAMMATORY SITES

[75] Inventors: Yorimasa Suwa; Atsushi Imaizumi; Masahiro Okada; Chieko Azuma; Ichiro Kudo; Keizo Inoue, all of Tokyo, Japan

[73] Assignee: Teijin Limited, Osaka, Japan

[21] Appl. No.: 861,962

[22] PCT Filed: Oct. 17, 1991

[86] PCT No.: PCT/JP91/01424

§ 371 Date: Jun. 18, 1992

§ 102(e) Date: Jun. 18, 1992

[87] PCT Pub. No.: WO92/06997

PCT Pub. Date: Apr. 30, 1992

[30] Foreign Application Priority Data

Oct. 18, 1990 [JP] Japan ................... 2-277842

[51] Int. Cl.$^5$ ................... A61K 37/02; C07K 7/10
[52] U.S. Cl. ................... 530/326; 530/324; 530/325
[58] Field of Search ................... 530/326, 325, 324; 514/13, 12

[56] References Cited

PUBLICATIONS

International Search Report, Dec. 12, 1991.
Hellman et al, "Amino Acid Sequence of the Trypsin-generated C3d Frgment from Human Complement Factor C3", Biochem. J. vol. 230, No. 2 (1985).
deBruijn et al., "Human Complement Component C3: cDNA Coding Sequence and Derived Primary Structure", Proc. Natl. Acad. Sci. U.S.A., vol. 82, No. 3 (1985).
Hellman et al, Biochem. J. 230, pp. 353–361 (1985).
Suwa et al, PNAS 87, 2395–2399 (1990).

*Primary Examiner*—Lester L. Lee
*Attorney, Agent, or Firm*—Sughrue, Mion, Zinn, Macpeak & Seas

[57] ABSTRACT

Peptide inhibitors of phospholipase $A_2$ from inflammatory sites having the amino acid sequence given in formula SEQ. I.D. NO: 1

[I]

Gln Lys Asp Ala Pro Asp His Gln Glu Leu Asn Leu Asp Val Ser
1               5                    10                 15
Leu Gln Leu Pro Ser Arg
                  20

1 Claim, 2 Drawing Sheets

PEPTIDE INHIBITORS OF PHOSPHOLIPASE A₂ PURIFIED FROM INFLAMMATORY SITES

TECHNICAL FIELD

The present invention relates to peptide inhibitors of phospholipase $A_2$ purified from inflammatory sites.

BACKGROUND ART

Phospholipase $A_2$ is an enzyme which hydrolyzes β-ester bonds in phospholipid to give fatty acids and lysophospho-lipids. Especially, it releases arachidonic acid which can be a precursor of prostaglandins, leukotriene, thromboxane and the like from membrane phospholipids and is thought to play an important role in the production of these inflammatory mediators. In recent years, phospholipase $A_2$ has been purified from the inflammatory sites of human inflammatory diseases and inflammatory model animals (it will be called phospholipase $A_2$ from inflammatory sites) and its properties have been clarified. This enzyme is thought to have the action to accelerate the inflammatory reactions, therefore the drug to inhibit the activity of this enzyme can be expected to reveal anti-inflammatory actions.

Complement C3 is a protein which has been known to perform the key functions in the complement pathway. C3 is hydrolyzed stepwise by a protease in blood. In other words, it is cleaved first with convertase into C3a an dC3b. C3b binds through its thiol ester site to the surface of activators followed by activation of the complement pathway to form a membrane attack complex. C3a works as an anaphylatoxin. At this time, a minor part of C3b binds to the activators, while the major part reacts with water to lose the binding activity, further undergoes hydrolysis by a protease to convert into C3dg or C3d finally.

The present inventors have already applied for patents after finding that human and rat C3dg inhibit specifically phospholipase $A_2$ purified from inflammation sites, succeeding in expression of rat C3 cDNA in *Escherichia coli* to produce a part of rat C3α chain (containing the C3dg part) as a recombinant protein, and realizing that the recombinant protein inhibits specifically phospholipase $A_2$ purified from inflammatory sites (PCT/J90/00996, W091/01999).

Human C3dg is, however, a protein of about 39 kDa molecular weight and it can be anticipated that the use of said protein as an anti-inflammatory as such will cause troubles in, for example, the transference to the affected part, the storage stability or antigenicity.

Thus, a novel peptide having inhibitory activity against phospholipase $A_2$ from inflammatory sites is desirably provided as an anti-inflammatory without such troubles.

Hereupon, the present inventors have made intensified studies in order to solve the above-mentioned problems to find that a part of the amino acid sequence of C3dg has action to inhibit phospholipase $A_2$, and attained the present invention.

DISCLOSURE OF THE INVENTION

In other words, the present invention is a peptide inhibitor of phospholipase $A_2$ purified from inflammatory sites having an amino acid sequence shown in SEQ ID No: 1.

Figure 1:
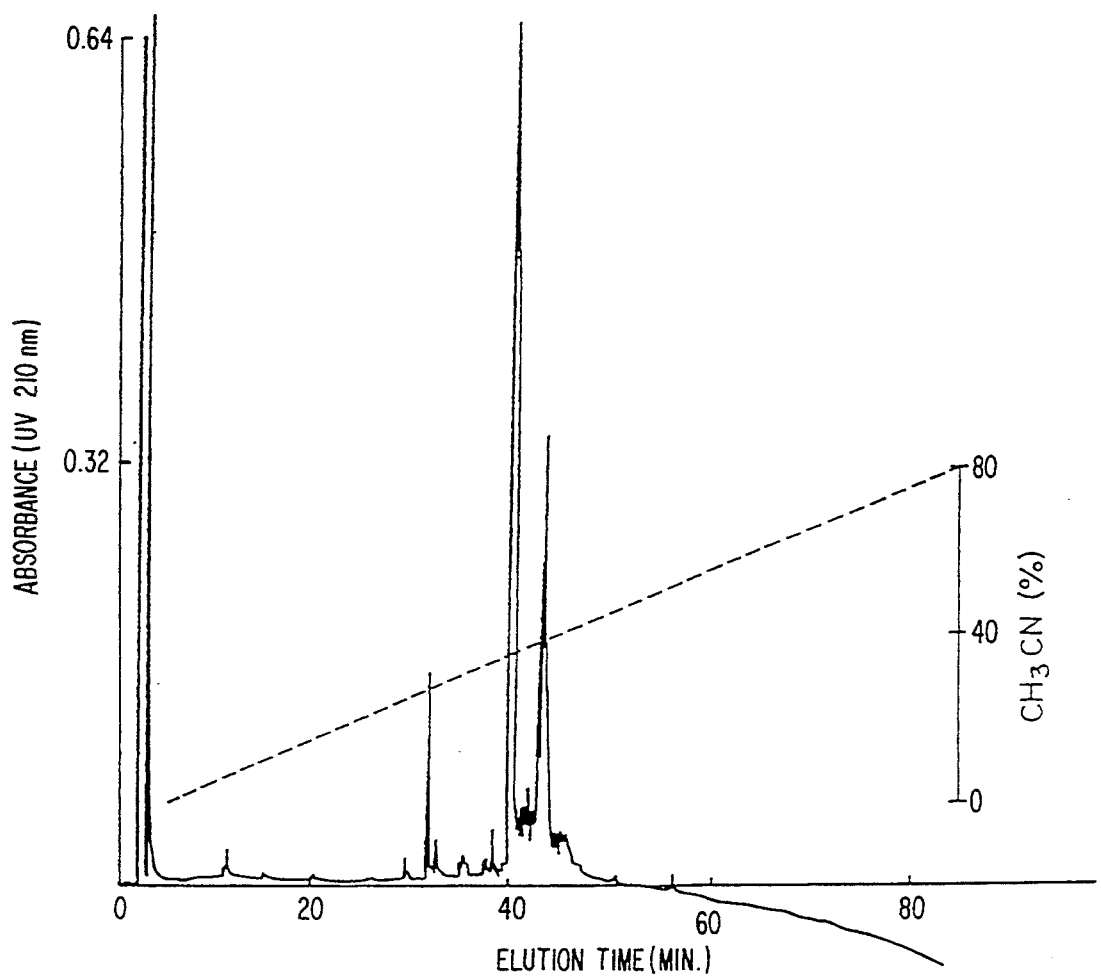
FIG. 1 gives the fractionation of the peptide in Example 1 according to the present invention by means of reversed phase HPLC.

In these figures, ●—● show the cases where the phospholipase $A_2$ purified from human inflammatory sites, ○—○ give the phospholipase $A_2$ from rat inflammatory sites and x—x show the phospholipase $A_2$ from procine pancreas.

BEST EMBODIMENT OF THE INVENTION

The peptides include the amino acid sequence of 21 residues shown in the SEQ ID No: 1. The amino acid sequence of said peptide is identical with the amino acid sequence from No. 612 to the C-terminus of human C3α chain. In the amino acid sequence in sequence No. 1, the peptides having substitution, deletion or insertion of one or more amino acid residues are also included in the peptides according to the present invention as long as they have the inhibitory activity against phospholipase $A_2$ from inflammatory sites.

Such peptides according to the present invention can be obtained by synthesis according to a customary procedure described in, for example, "The basis and experiments in peptide syntheses" (written in Japanese); N. Izumiya, T. Kato, H. Aoyagi and M. Yaki: Maruzen, Tokyo) or E. Atherton, R.C. Sheppard; "Solid phase peptide synthesis, a practical approach" (LRL press) followed by purification. Or human C3α chain or the like is used as a starting substance to be hydrolyzed with an enzyme such as α-chymotrypsin.

The peptide synthesis, the measurement of the inhibitory activity against phospholipase $A_2$ or the like used in the present invention will be illustrated in the following:

①Peptide Synthesis and Purification

A peptide synthesizer 431A of Applied Biosystem was employed to conduct the synthesis by the Fmoc method.

The deprotection of the samples was carried out by the TMSBr cleavage method according to the protocol of Applied Biosystem.

The samples were purified by using the reversed phase HPLC column (Vydac Protein $C_{18}$, 2.2 cm ID×25 cm L) and eluted with the gradient of 0 to 80% acetontrile in the presence of 0.1% trifluoroacetic acid.

②Determination of Inhibitory Activity Against Phospholipase $A_2$

The activity-measuring system was prepared by adding distilled water to 100 mM Tris-HCl (ph 9.0), 4 mM calcium chloride, 0.1 mM phosphatidylethanolamine (2,000 dpm/nmol), and 10 μl sample to adjust the total volume to 240 μl, and finally 10 μl of 0.1 ng/μl phospholipase $A_2$ was added. The phospholipases $A_2$ used were from human inflammatory sites (the joint fluid from patients with rheumatoid arthritis) (Hara et al., J. Biochem., 104, 326–328, 1988), rat inflammatory sites (Chang et al., J. Biochem., 102, 147–154, 1987), and porcine pancreas (Boehringer Manheim Co.). Phosphatidylethanolamine was purified from *Escherichia coli* cultured in a medium to which acetic acid was added.

The reactions were conducted at 37° C. with stirring for 10 minutes. The termination of the reaction and the extraction of fatty acids generated were carried out by the Dole's method (Dole et al., J. Biol. Chem., 235, 2595-2599, 1960) and the extracted fatty acid was determined with a scintillation counter.

The present invention will be illustrated in more detail by examples.

EXAMPLE 1

Synthesis and Purification of the Peptides Having Inhibitory Activity Against Phospholipase $A_2$ from Inflammatory Sites A peptide was synthesized in accordance with the amino acid sequence given in SEQ. ID No: 1 using a peptide synthesizer (Applied Biosystem, 413 A). The yield was 77.9%.

After deprotection, the 140.7 mg crude product was fractionated with reversed phase HPLC (FIG. 1). the main peak eluted with about 35% acetonitrile was collected and lyophilyzed. The yield of the finally purified sample was 21.8 mg. The sample was confirmed to have the amino acid sequence of No. 1 by a gas-phase protein sequencer 477 A of Applied Biosystem.

tion was further diluted stepwise with the same buffer and the inhibitory activity of phospholipase $A_2$ from inflammatory sites was determined at individual concentrations.

Figure 2:
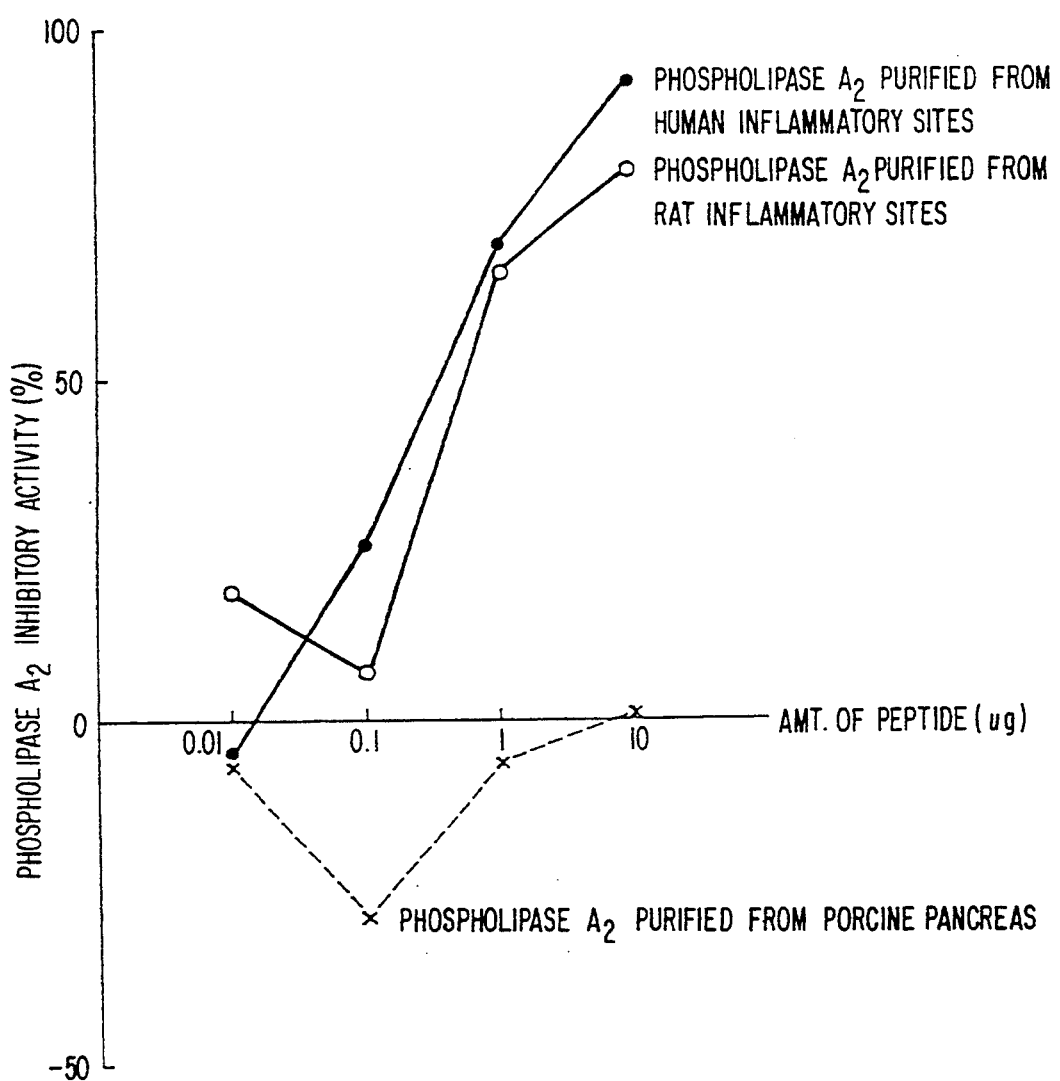
FIG. 2 gives the inhibitory activity of the peptide according to the present invention against phospholipase $A_2$, which was determined in Example 2.

The results are given in FIG. 2. The peptide according to the present invention inhibited phospholipase $A_2$ from human inflammatory sites (●—●) and phospholipase $A_2$ from rat inflammatory sites (○—○) does-dependently. In both enzymes, the amount of the protein needed for 50% inhibition of 1 ng enzyme activity was about 300 ng and $IC_{50}$ was about $5 \times 10^{-7}$ M. Meanwhile, it showed no inhibitory activity against phospholipase $A_2$ from porcine pancreas (x—x).

FIELD OF INDUSTRIAL UTILITY

Peptide inhibitors of phospholipase $A_2$ from inflammatory sites according to the present invention have inhibitory activity against phospholipase $A_2$ from the inflammatory sites and are expected to have an action to inhibit allergic reactions, and can be utilized as an anti-inflammatory and a therapeutic agent for allergic diseases in mammalians especially in human. Additionally, they are expected to have excellent in vivo transference to the affected parts and high storage stability.

---

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:1:

```
Gln Lys Asp Ala Pro Asp His Gln Glu Leu Asn Leu Asp Val Ser Leu
 1               5                  10                  15
Gln Leu Pro Ser Arg
            20
```

EXAMPLE 2

Phospholipase $A_2$ Inhibitory Acitivity

The lyophilyzed sample obtained in Example 1 was dissolved again in 50% acetone-0.1% trifluoroacetic acid to adjust the concentration to 10 mg/ml. The solu-

We claim:

1. A purified peptide inhibitor of phospholipase $A_2$, consisting essentially of the amino acid sequence represented in SEQ ID No:1.

* * * * *